US011723727B2

(12) United States Patent
Wittnebel et al.

(10) Patent No.: US 11,723,727 B2
(45) Date of Patent: Aug. 15, 2023

(54) SYSTEM FOR PERFORMING EYE SURGERY WITH SIMULTANEOUS DISPLAY OF GRAPHICAL INFORMATION FOR FLAP AND ABLATION

(71) Applicant: Alcon Inc., Fribourg (CH)

(72) Inventors: Michael Wittnebel, Hirschaid (DE); Mario Abraham, Burgthann (DE); Stefan Schmid, Neuendettelsau (DE); Maik Lange, Rückersdorf—Entensee (DE); Martin Starigk, Nuremberg (DE)

(73) Assignee: Alcon Inc., Fribourg (CH)

( * ) Notice: Subject to any disclaimer, the term of this patent is extended or adjusted under 35 U.S.C. 154(b) by 626 days.

(21) Appl. No.: 16/090,053

(22) PCT Filed: Apr. 4, 2016

(86) PCT No.: PCT/IB2016/051906
§ 371 (c)(1),
(2) Date: Sep. 28, 2018

(87) PCT Pub. No.: WO2017/175026
PCT Pub. Date: Oct. 12, 2017

(65) Prior Publication Data
US 2019/0105111 A1    Apr. 11, 2019

(51) Int. Cl.
*A61F 9/008* (2006.01)
*A61B 34/00* (2016.01)
*A61B 34/10* (2016.01)
*A61B 17/00* (2006.01)

(52) U.S. Cl.
CPC .......... *A61B 34/25* (2016.02); *A61F 9/00804* (2013.01); *A61F 9/00836* (2013.01); *A61B 2017/00199* (2013.01); *A61B 2034/107* (2016.02); *A61B 2034/252* (2016.02); *A61B 2034/256* (2016.02); *A61F 2009/00844* (2013.01); *A61F 2009/00855* (2013.01); *A61F 2009/00872* (2013.01); *A61F 2009/00878* (2013.01); *A61F 2009/00887* (2013.01)

(58) Field of Classification Search
CPC ................. A61F 2009/00872; A61F 9/00836
See application file for complete search history.

(56) References Cited

U.S. PATENT DOCUMENTS

| | | | | |
|---|---|---|---|---|
| 6,129,722 A | * | 10/2000 | Ruiz | A61F 9/008 351/212 |
| 6,694,173 B1 | * | 2/2004 | Bende | A61B 5/0095 600/407 |
| 2002/0007177 A1 | | 1/2002 | Campin et al. | |
| 2014/0135747 A1 | * | 5/2014 | Donitzky | A61F 9/00827 606/4 |
| 2015/0247199 A1 | * | 9/2015 | Fletcher | C12Q 1/6883 506/9 |
| 2017/0360297 A1 | * | 12/2017 | Yun | A61B 3/1025 |

FOREIGN PATENT DOCUMENTS

| | | | | |
|---|---|---|---|---|
| CA | 2707522 A1 | * | 7/2009 | A61B 3/132 |
| CA | 2840496 A1 | * | 1/2013 | A61B 34/20 |

* cited by examiner

*Primary Examiner* — Michael J D'Abreu

(57) ABSTRACT

The disclosure relates to systems and methods for performing eye surgery in which a single image that simultaneously presents a graphical representation of a planned or actual flap location superimposed with a graphical representation of a planned or actual area of ablation is used.

21 Claims, 4 Drawing Sheets

SYSTEM FOR PERFORMING EYE SURGERY WITH SIMULTANEOUS DISPLAY OF GRAPHICAL INFORMATION FOR FLAP AND ABLATION

TECHNICAL FIELD

The present disclosure relates to a system for performing eye surgery in which a flap is cut and tissue underlying the flap is then ablated.

BACKGROUND

Refractive eye surgery is commonly used to correct a variety of vision problems. One common such refractive surgery is known as LASIK (laser-assisted in situ keratomileusis) and is used to correct myopia, astigmatism, or more complex refractive errors. Other eye surgeries may correct corneal defects or other problems. For instance phototherapeutic keratectomy (PTK) may be used to remove diseased corneal tissue or corneal irregularities either alone or in combination with LASIK. These surgeries may be used alone, but some are also compatible with other vision correction surgeries, such as cataract surgery. For instance, LASIK to correct astigmatism is often combined with cataract surgery.

During LASIK and other eye surgeries, corrective procedures are commonly performed on interior parts of the eye, such as the corneal stroma, rather than on the eye surface. This practice tends to improve surgical outcomes by allowing the corrective procedure to be targeted to the most effective part of the eye, by keeping the outer, protective parts of the eye largely intact, and for other reasons.

The interior part of the eye may be accessed in a variety of manners, but frequently access involves cutting a flap in the cornea. This is particularly true for eye surgeries, such as LASIK, where the corrective procedure is performed on an interior part of the cornea, such as the stroma. The flap allows an outer part of the cornea, forming the flap, to be lifted and folded out of the way, permitting access to the interior part of the cornea. The flap is commonly cut mechanically using a microkeratome or a laser. After the cornea is cut, the flap will typically be pulled back over a hinge of corneal tissue that connects the flap to the eye to expose an interior part of the cornea. This interior part of the cornea may be shaped to correct myopia, astigmatism, or other refractive errors, or to remove undesirable tissue such as diseased or irregular tissue. Often, the shaping or tissue removal is done through corneal ablation with a laser, such as an excimer laser.

SUMMARY

The present disclosure relates to a surgery system for performing eye surgery. The system includes a cutting device for cutting a flap in a cornea of an eye undergoing eye surgery, a shaping device performing ablation of an interior part of the cornea, and at least one display for displaying a single image that simultaneously presents a graphical representation of a planned or actual flap location superimposed with a graphical representation of a planned or actual area of ablation.

The present disclosure also relates to a method for performing eye surgery. The method includes receiving information derived from an examination of the eye undergoing surgery into a surgery system, using the information to generate a single image that simultaneously presents a graphical representation of a planned or actual flap location superimposed with a graphical representation of a planned or actual area of ablation, adjusting a planned flap location parameter or a planned area of ablation parameter if an inconsistency in the planned or actual flap location and the planned or actual area of ablation is identified and generating a new single image, cutting a flap in a cornea of the eye that allows access to an interior part of the cornea if the planned or actual flap location and the planned or actual area of ablation are consistent, and performing ablation of the interior part of the cornea in the planned or actual area of ablation.

The above system may be used with the above method and vice versa.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

In current surgery systems, the device for cutting the flap is typically separate from that for performing the ablation. These devices are controlled through separate interfaces such that a user must plan and cut the flap on one interface and plan and perform the ablation on a separate interface. The use of separate interfaces increases the likelihood of user error and the likelihood of flaps that are improperly sized or placed for the planned ablation.

Newer systems are now able to both cut the flap and perform the ablation using the same system that combines the devices used. However, in these systems, the separate stages of the surgery are still planned separately. For instance, a refractive profile to be achieved by ablation is first planned, and then a flap to fit the refractive profile is designed later.

The flap is cut to accommodate the intended corneal ablation. A flap of the wrong size or shape or in the wrong position may interfere with the ablation and may result in adverse complications such glare, haze, ghost images, or other distortions of the visual field. If the flap is determined to be improperly sized or placed, the surgery may need to be terminated, with the patient being given multiple months to heal before another attempt at refractive surgery is made. In order to avoid such complications, many surgeons cut a very large flap, which may give rise to other problems and may increase healing time.

The present disclosure relates to a system and method for performing eye surgery, such as LASIK, in which the same device that is used to plan cutting the flap or ablation is also used to perform cutting the flap or ablation. In addition, the system and method may be used to provide all graphical information regarding the flap location and the area of ablation displayed simultaneously in a single image on a display. This information is provided before performing the procedure, although updated information may be provided during the procedure as well. For instance, the system and method may also display multiple types or iterations of a single image that simultaneously presents graphical information regarding the flap location and the area of ablation.

Figure 1:
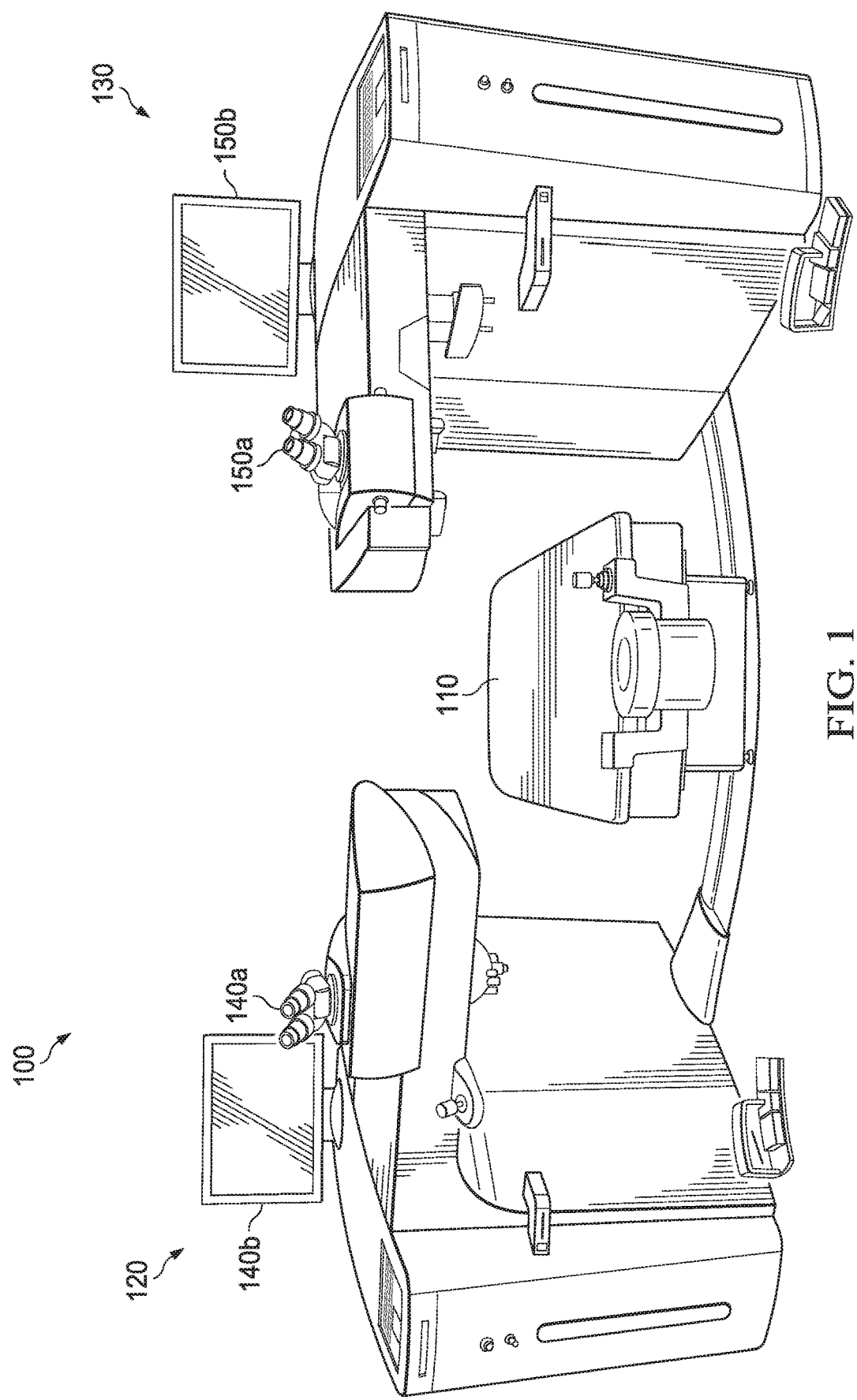
FIG. 1 is a schematic diagram of a system for performing refractive eye surgery.

In addition, the system and method may display the single image on one display, or they may display the same single image on more than one display simultaneously or at different times. FIG. 1 is a schematic diagram of a surgery system 100 for performing refractive surgery. The system 100 includes a support 110 for positioning a patient, a cutting device 120 for cutting a flap in the cornea of a patient's eye, and a shaping device 130 for performing ablation on an interior part of the cornea. FIG. 1 further includes cutting device displays 140a, which is a microscope display, and 140b, which is a screen, as well as shaping device displays 150a, which is a microscope display, and 150b, which is a screen.

Cutting device 120 may include a laser, such as a femtosecond laser, which uses short laser pulses to ablate a series of small portions of corneal tissue to form a flap that may be lifted up to expose an interior part of the cornea. The flap may be planned and cut using one or both of cutting device displays 140, along with control devices and a computer.

Shaping device 130 may include a laser, such as an excimer laser, which ablates corneal tissue in the area of ablation of the exposed interior part of the cornea using laser pulses. The area of ablation may be planned an ablated using one or both of shaping device displays 150, along with control devices and a computer.

Cutting device 120 and shaping device 130 may be physically separated as shown in FIG. 1. The patient may be moved between cutting device 120 and shaping device 130. Alternatively, the patient may remain stationary and the cutting device 120 or the shaping device 130 may be moved to the patient. In other embodiments, the cutting device 120 and shaping device 130 may be physically combined into a single unitary device, such that neither the device nor the patient is repositioned when switching from cutting device 120 and shaping device 130.

The system 100 also includes one or more control devices for controlling cutting device 120 and shaping device 130. The control devices may include an interactive display, such as a touchscreen display, a keyboard, a mouse, a touchpad, buttons, a joystick, a foot pedal, a heads-up display, virtual-reality glasses, or other devices able to interact with a user.

System 100 further includes at least one computer able to generate an image presented on at least one of displays 140 or 150. The computer may be further connected to observational devices, such as a microscope, a camera, an optical coherence tomography (OCT) device or display, or another device able to measure the position of the eye undergoing surgery. The computer may further be connected to one or more of the control devices.

In one example, the same cutting device computer i) is connected to observational devices that observe the eye when the patient is positioned with cutting device 120, ii) sends graphical information regarding the planned flap location and the planned area of ablation to a cutting device display 140, and iii) is connected to cutting device control devices.

In another example, the same shaping device computer i) is connected to observational devices that observe the eye when the patient is positioned with shaping device 130, ii) sends graphical information regarding the planned flap location and the planned area of ablation to a shaping device display 150, and iii) is connected to shaping device control devices.

In still another example, the same computer has all of the properties described above with respect to both the cutting device computer and the shaping device computer.

Any computer in system 100 may connect to another part of system 100 via a wired connection or wirelessly. One of more of computers of system 100 may also be connected to a database, stored locally, on a remote server, or both that store patient data, treatments plans, or other information useful in the eye surgery.

System 100 may automatically enter information regarding a patient and the treatment to be performed on that patient or actually performed on that patient. System 100 may allow a user to enter and view information regarding a patient and the treatment to be performed on that patient. Such data may include information about the patient, such as identifying information, the patient's medical history, and information about the eye or eyes being treated. Such data may also include information about the treatment plans, such as the shape and location of the corneal cut and the location and degree of corneal ablation.

Figure 2:
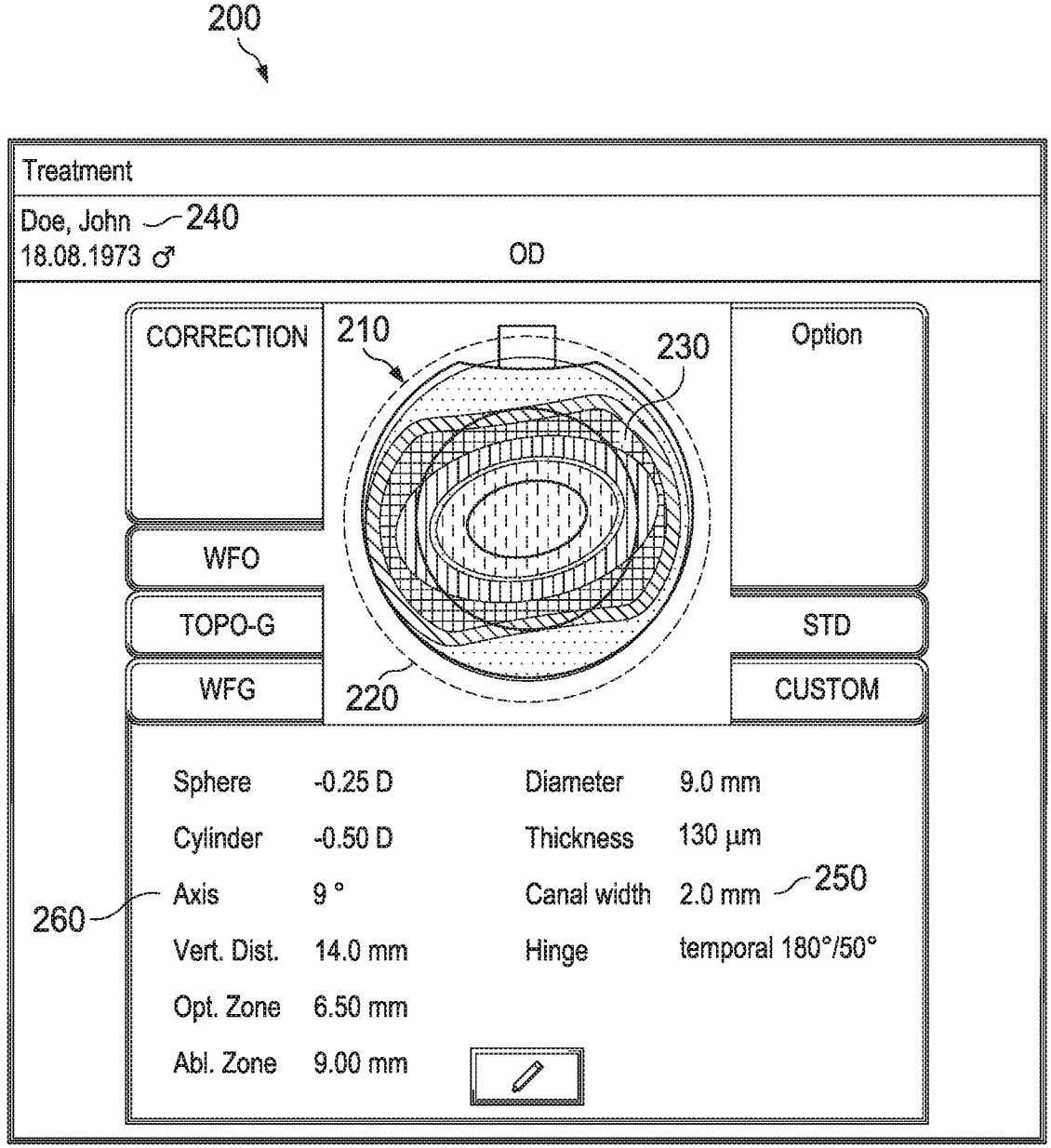
FIG. 2 is a schematic diagram of an exemplary interface display of one eye for planning and performing refractive eye surgery using the system of FIG. 1.

FIG. 2 is an example image 200 of one eye that may be displayed on a screen display 140b or 150b in system 100. Image 200 includes a simultaneous graphical representation 220 of the planned flap location, as well as a graphical representation 230 of the planned area of ablation in the same eye image 210. As a result, the relative locations of the planned flap location and the planned area of ablation may be readily visually compared. This allows the user to ensure that the flap is in the correct location for ablation without having to cut an overly large flap.

Graphical representation 220 may include other information regarding the flap in addition to the flap location. Similarly, graphical representation 230 may include other information regarding ablation in addition to the area of ablation. For instance, in the example of eye image 210, graphical representation 230 is a heat map with different colors represented planned ablation locations.

Eye image 210 may include other graphical information regarding the eye, such as the optical zone, location or size of the pupil, or location or size of the iris.

Image 200 may contain information regarding the eye or the planned eye surgery other than eye image 210. Image 200 may further contain information regarding the patient, such as a name 240.

Image 200, when presented prior to cutting the flap, may include textual flap information 250 for displaying and editing the parameters of the flap. These parameters may include, for example, the side angle of the cut, the diameter and thickness of the flap, the position and size of the flap hinge, and the size of a ventilation canal. The flap and hinge parameters may be adjusted through one or more input devices, which may be the same as or separate from control devices. As the flap and hinge parameters are adjusted, the graphical representation 220 of the flap is adjusted to accurately represent the currently entered parameters. Alternatively, system 100 may allow adjustments by using an input device to manipulate graphical representation 220.

Image 200, when presented prior to ablation, may also include textual information 260 for displaying and editing the parameters of the ablation. These parameters may be presented in terms of the planned correction to near- or far-sightedness or to astigmatism. Such planned correction may be presented as sphere, cylinder, and axis parameters. The parameters may also include a specification of the size of the area ablation and may be presented as sizes for a planned optical zone and a planned ablation zone. The parameters may be adjusted through one or more input devices, which may be the same as or separate from control devices. As the ablation parameters are adjusted, the graphical representation 230 may be adjusted to accurately represent the currently entered parameters. Alternatively, system 100 may allow adjustments by using an input device to manipulate graphical representation 230.

During eye surgery, between cutting the flap and ablation, an alternative image similar to image 200 may be presented. This image may include a graphical representation of the actual flap location and, simultaneously, a graphical representation of the planned area of ablation. A graphical representation of the planned flap location may also be presented. Such an image may allow the user to evaluate whether the actual flap location is sufficiently similar to the planned flap location, whether the actual flap location is sufficient to allow the planned ablation, or to otherwise evaluate whether it is appropriate to proceed with ablation.

Similarly, after eye surgery or after ablation, another alternative image similar to image 200 may be presented. This image may include a graphical representation of the actual area of ablation or other actual ablation information and, simultaneously, a graphical representation of the planned or actual flap location. A graphical representation of the planned area of ablation or other planned ablation information may also be presented. Such an image may allow the user to evaluate whether the surgery proceeded as planned, whether any additional ablation is needed, and any effects of deviations from the planned flap location, planned area of ablation, or other planned ablation information. For instance, some deviations from the planned area of ablation may be corrected immediately by performing additional ablation.

Image 200 or other images as described above may include a schematic, photographic, or video image of the actual eye and may be overlaid on the eye image 210.

Although image 200 is a top-down view, images according to the present disclosure may be from other angles or points of view. For instance, the image may be a profile or cross-sectional view.

By simultaneously presenting graphical information regarding the flap location and the area of ablation, system 100 allows the user to more readily identify inconsistencies between planned or actual flap location and area of ablation. Particularly before cutting the flap or performing ablation, or even after cutting the flap, but before ablation, identifying inconsistencies may allow corrective actions to improve surgical outcome. Even if only actual inconsistencies are identified, corrective actions may still be possible, or post-operative treatments may be improved.

In order to take further advantage of the ability to identify inconsistencies using an image presented by system 100, the image or another component of system 100 may alert the user to potential inconsistencies between flap location, area of ablation, or other ablation information. For example, the image presented may alert the user to a potential inconsistency using color, icons, dialog boxes, sounds, or other warnings.

Figure 3:
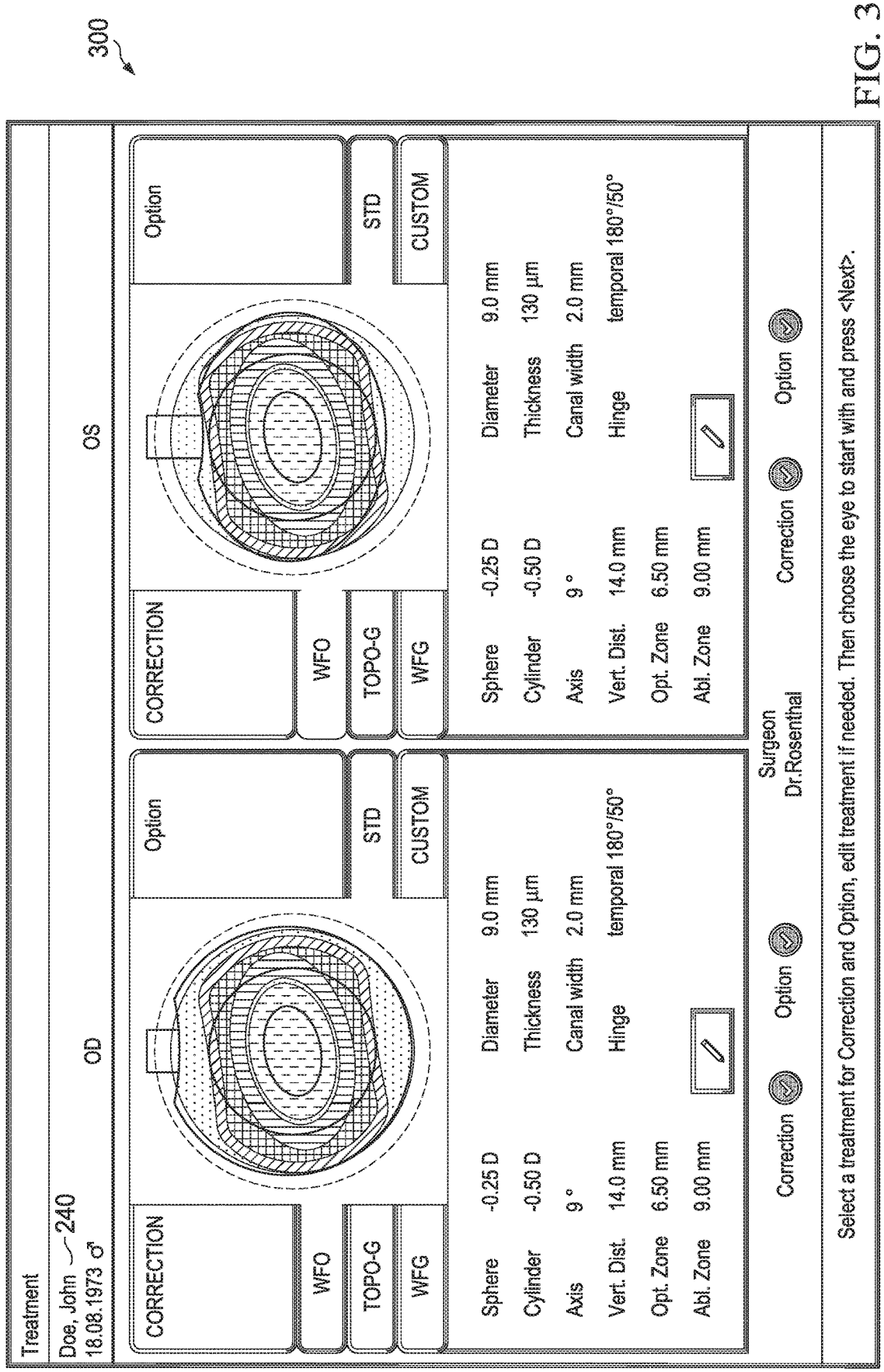
FIG. 3 is a schematic diagram of an exemplary interface display of both eyes for planning and performing refractive eye surgery using the system of FIG. 1.

FIG. 3 is an example image 300 of both eyes that may be presented on a screen display 140b or 150b in system 100.

Figure 4:
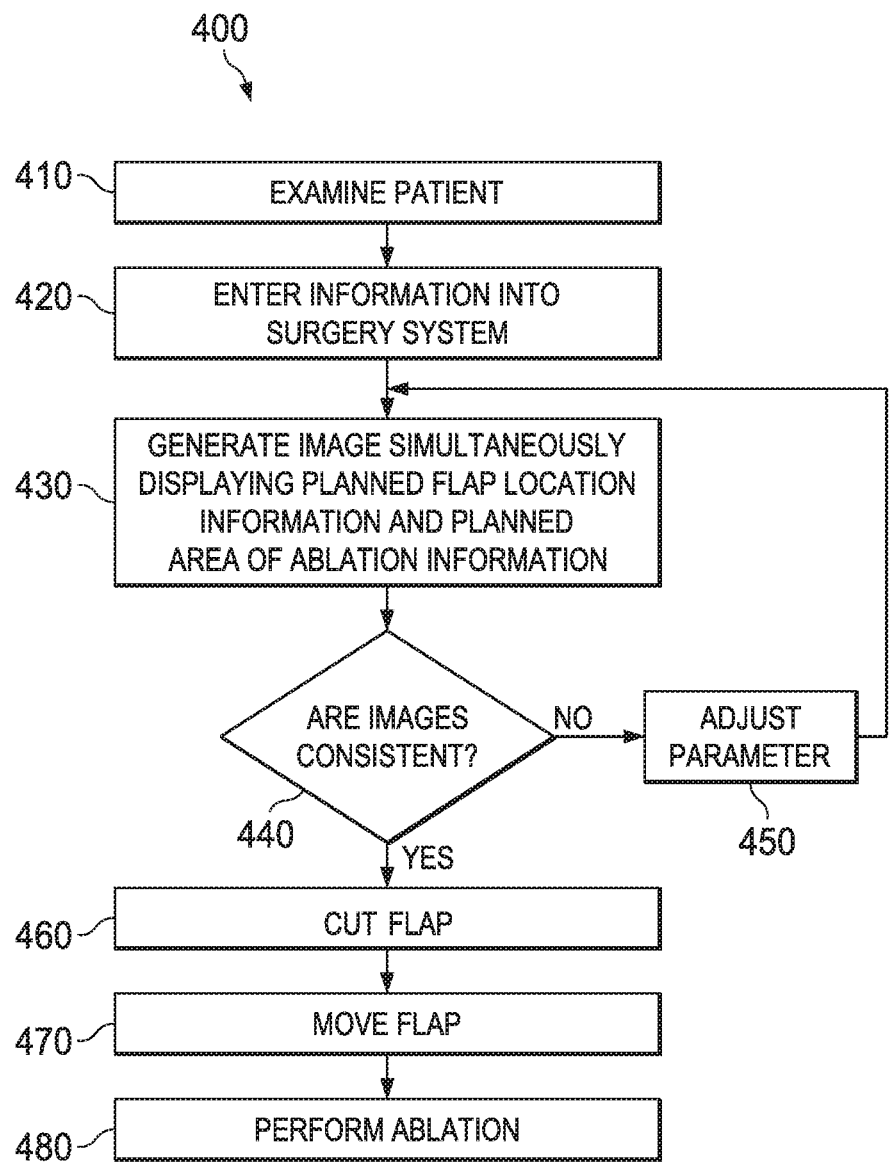
FIG. 4 is a flowchart of a method for performing eye surgery using a single image that simultaneously presents graphical information regarding the flap location and the area of ablation.

FIG. 4 is a flowchart of a method 400 for performing eye surgery using a single image that simultaneously presents graphical information regarding the flap location and the area of ablation. In step 410, at least one of the patient's eyes is examined to identify and determine the parameters of visual or eye defects.

In step 420, information derived from the examination is entered into a surgery system. In step 430, an image of at least one eye containing graphical information regarding flap location and the area of ablation in a planned surgery is generated and a single image simultaneously presenting this information is produced.

In step 440, the image is evaluated for consistency of the planned flap location and the planned area of ablation. If the planned flap location and area of ablation are not consistent, then an adjustment to a planned flap location parameter or a planned area of ablation parameter is made in step 450 and a new image is generated.

If the planned flap location and area of ablation are consistent, then a flap is cut in step 460.

The flap is them moved to allow access to an interior part of the cornea in step 470.

Next, in step 480, ablation is performed in the area of ablation.

The process may include other steps in addition to those described above. For instance, after step 460, the graphical information regarding actual flap location may be determined and presented simultaneously with the graphical information regarding planned area of ablation. Graphical information regarding the planned flap location may also be presented simultaneously.

After step 480, graphical information regarding the actual flap location or planned flap location may be presented simultaneously with graphical information regarding the actual area of ablation. Graphical information regarding the planned area of ablation may also be presented simultaneously.

The images referred to in method 400 may also be presented on one or more different displays at the same time or as surgery progresses. For instance, if the surgery is refractive eye surgery, the image in step 430 may be presented on a display associated with a cutting device, such as a femtosecond laser, while the image may be presented on a different display associated with a shaping device, such as an excimer laser, after step 460, but before or during step 480.

In addition, in some procedures the steps of method 400 may involve additional activities. For instance, examination of step 410 may include, for example, a determination of the size and shape of the iris and pupil, the thickness and shape of the cornea, the identification of diseased or irregular corneal tissue, or the desired vision correction.

During or following the examination, the user may enter and edit parameters of the planned flap position, such as, the side angle of the cut, the diameter and thickness of the flap, and the position and size of the flap hinge. During of following the examination, the user may also enter and edit parameters regarding ablation such as the desired correction to near- or far-sightedness or to astigmatism, and a specification of the size of the area to be ablated.

During step 430 or during or in addition to any later steps, a user may be alerted to any inconsistencies in the planned surgery, such as in the planned flap location and planned area of ablation.

The disclosed systems and methods may be used in LASIK procedures as well as other procedures such as LASEK, epi-LASIK, trans-epi-LASIK, PKT, photorefractive keratectomy (PRK), cataract surgery, and the like, as well as combinations of such procedures.

In addition, variations of the disclosed systems and methods may be used in other procedures in which corneal tissue is simply removed, such as PTK with shaping afterwards.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A surgery system for performing eye surgery comprising:
   a cutting device comprising a laser configured to cut a flap in a cornea of an eye undergoing eye surgery;
   a shaping device comprising a laser configured to perform ablation of an interior part of the cornea;
   at least one display configured to:
      display a single image that simultaneously presents a graphical representation of a planned or actual flap location superimposed with a graphical representation of a planned area of ablation, the single image showing the planned flap location relative to the planned area of ablation, the graphical representation of the planned flap location associated with a plurality of flap parameters, the graphical representation of the planned area of ablation associated with a plurality of ablation parameters, the planned area of ablation comprising a plurality of ablation locations, the graphical representation of the planned area of ablation comprising a heat map of the planned area of ablation that represents each ablation location with a different color; and
   a computer configured to:
      receive an adjustment of the flap parameters;
      adjust the planned flap location relative to the planned area of ablation shown in the single image by adjusting the graphical representation of the planned flap location according to the adjusted flap parameters;
      receive an adjustment of the ablation parameters; and
      adjust the planned area of ablation relative to the planned flap location shown in the single image by adjusting the map of the planned area of ablation according to the adjusted ablation parameters.

2. The system of claim 1, wherein the single image further comprises textual information regarding the flap.

3. The system of claim 2, wherein the textual information regarding the flap comprises textual information regarding at least one of the side angle of the cut, flap diameter, flap thickness, hinge size, or hinge location.

4. The system of claim 1, wherein the single image further comprises textual information regarding the ablation.

5. The system of claim 4, wherein the textual information regarding the ablation comprises textual information regarding at least one of sphere, cylinder, or axis.

6. The system of claim 1 wherein the plurality of ablation parameters comprise a size of the planned area of ablation.

7. The system of claim 6 wherein the size of the planned area of ablation is presented as a planned optical zone and a planned ablation zone.

8. The system of claim 1, wherein the laser configured to cut the flap comprises a femtosecond laser.

9. The system of claim 1, wherein the laser configured to perform ablation comprises an excimer laser.

10. The system of claim 1, wherein the single image simultaneously presents a graphical representation of an actual flap location superimposed with the graphical representation of the planned flap location and the graphical representation of the planned area of ablation.

11. The system of claim 1, wherein the single image simultaneously presents a graphical representation of an actual ablation area superimposed with the graphical representation of the planned flap location and the graphical representation of the planned area of ablation.

12. The system of claim 1, wherein the single image simultaneously presents a graphical representation of an actual flap location and an actual ablation location superimposed with the graphical representation of the planned flap location and the graphical representation of the planned area of ablation.

13. The system of claim 1, wherein the image further presents graphical information regarding the optical zone, the location or size of the pupil, or the location or size of the iris.

14. The system of claim 1, wherein the at least one display comprises at least one cutting device display and at least one separate shaping device display, and the single image is displayed on one or both of the at least one cutting device display and the at least one separate shaping device display.

15. The system of claim 1, wherein the image comprises an alert if a potential inconsistency between the planned or actual flap location and the planned or actual area of ablation is identified by the system.

16. The system of claim 1 wherein the graphical representation of the planned or actual flap location further comprises a perimeter of the planned or actual flap.

17. The system of claim 1 wherein the single image further comprises sphere, cylinder, and axis parameters.

18. The system of claim 1 wherein the graphical representation of the planned or actual area of ablation further comprises a size of a planned optical zone and a size of a planned ablation zone.

19. The system of claim 1 wherein the at least one display is configured to:
   overlay a video of the eye undergoing eye surgery onto the single image.

20. The system of claim 1 wherein the laser configured to cut the flap and the laser configured to perform ablation is the same laser.

21. The system of claim 1 wherein the laser configured to cut the flap and the laser configured to perform ablation are different lasers.

* * * * *